United States Patent
Ryan

(10) Patent No.: US 9,039,750 B2
(45) Date of Patent: May 26, 2015

(54) HANDLE CONTROL SYSTEM FOR A STENT DELIVERY SYSTEM

(75) Inventor: Michael Ryan, Limerick (IE)

(73) Assignee: Cook Medical Technologies LLC, Bloomington, IN (US)

( * ) Notice: Subject to any disclaimer, the term of this patent is extended or adjusted under 35 U.S.C. 154(b) by 23 days.

(21) Appl. No.: 13/311,880

(22) Filed: Dec. 6, 2011

(65) Prior Publication Data

US 2012/0158117 A1 Jun. 21, 2012

Related U.S. Application Data

(60) Provisional application No. 61/423,691, filed on Dec. 16, 2010.

(51) Int. Cl.
*A61F 2/06* (2013.01)
*A61F 2/966* (2013.01)
*A61F 2/95* (2013.01)

(52) U.S. Cl.
CPC .......... *A61F 2/966* (2013.01); *A61F 2002/9517* (2013.01)

(58) Field of Classification Search
CPC ........................ A61F 2/966; A61F 2002/9517
USPC .................. 606/1, 108, 190–194, 196–199; 623/1.11, 1.12, 1.23, 2.11
See application file for complete search history.

(56) References Cited

U.S. PATENT DOCUMENTS

| | | | |
|---|---|---|---|
| 4,655,771 A | | 4/1987 | Wallsten |
| 4,762,128 A | * | 8/1988 | Rosenbluth ................... 606/192 |
| 5,222,971 A | * | 6/1993 | Willard et al. ................ 606/198 |
| 6,190,360 B1 | | 2/2001 | Iancea et al. |
| 2003/0191516 A1 | | 10/2003 | Weldon et al. |
| 2005/0273151 A1 | * | 12/2005 | Fulkerson et al. ........... 623/1.11 |
| 2009/0024133 A1 | | 1/2009 | Keady et al. |
| 2009/0326549 A1 | * | 12/2009 | Wolfe ........................... 606/127 |
| 2010/0004606 A1 | * | 1/2010 | Hansen et al. ................ 604/264 |
| 2010/0168834 A1 | | 7/2010 | Ryan et al. |
| 2010/0217187 A1 | * | 8/2010 | Fulkerson et al. ......... 604/96.01 |

FOREIGN PATENT DOCUMENTS

DE 297 17 110 U1 1/1998

OTHER PUBLICATIONS http://www.thefreedictionary.com/tension, dictionary definition of the term tension retrieved on Sep. 4, 2013.*
www.thefreedictionary.com/direction, definition of the term direction, retrived Apr. 7, 2014.*
International Search Report mailed Apr. 11, 2012 for International Application No. PCT/US2011/063381.
Written Opinion mailed Apr. 11, 2012 for International Application No. PCT/US2011/063381.

* cited by examiner

*Primary Examiner* — David Eastwood
(74) *Attorney, Agent, or Firm* — Brinks Gilson & Lione

(57) ABSTRACT

A control system for controlling movement of a medical device delivery system, a stent delivery system and a method for controlling movement of a medical device delivery system are provided. The control system includes a rotatable gear operably connected to a first movable member and a second movable member movable by the rotatable gear. The first movable member is operably connected to the first shaft and the second movable member operably connected to the second shaft. The first movable member moves the first shaft and the second movable member moves the second shaft to change a position of the first shaft relative to the second shaft and to change a configuration of a medical device operably connected to the first shaft and the second shaft.

20 Claims, 7 Drawing Sheets

HANDLE CONTROL SYSTEM FOR A STENT DELIVERY SYSTEM

RELATED APPLICATIONS

This application claims the benefit of U.S. Provisional Application No. 61/423,691, filed Dec. 16, 2010, which is incorporated by reference herein in its entirety.

TECHNICAL FIELD

This invention relates to a medical device and, in particular to a handle control system for a device for delivering and deploying a stent and a method of controlling the stent delivery system.

BACKGROUND

A self-expanding stent is typically introduced into the body using a delivery device that includes an outer sheath coaxially disposed and slidable over an inner catheter. The stent is disposed at the distal end of the device between the inner catheter and the outer sheath and held in a compressed position by the outer sheath. The inner catheter and the outer sheath move coaxially with respect to each other. The stent may be deployed by proximally pulling back the outer sheath relative to the inner catheter until the stent is exposed. The self-expanding stent expands from the stent distal end to the stent proximal end as the sheath is proximally withdrawn.

Several problems may occur with the sheathed delivery device described above. The sheath release delivery devices are difficult to reposition or remove and slow to operate. The stent may only be partially deployed prior to reconstrainment of the stent by the sheath in order to still reposition or remove the stent. Once the stent is fully deployed, i.e. radially expanded, the sheath cannot reconstrain the stent. For example, utilizing a conventional outer sheath/inner catheter delivery device may cause the physician to inadvertently use excessive force and pull back the outer sheath too far, thereby prematurely deploying the stent in an incorrect position within a body lumen. At this step in the procedure, repositioning of the stent becomes difficult, if not impossible, because the stent has already radially self-expanded into the body lumen.

Additionally, in a typical sheath release device where the outer sheath is proximally withdrawn, the first portion of the self-expanding stent to make contact with the body vessel is the most distal portion of the stent. This type of release may cause difficulty in accurately placing the proximal portion of the stent because the distal end of the stent is positioned first while the proximal portion of the stent is still covered by the outer sheath. Accurate placement of the proximal portion of the stent and/or the stent body may be important in certain applications, for example to prevent stent migration or to properly open a stricture along the entire length of the stricture. An additional drawback occurs with the sheathed stent delivery system where direct visualization of the stent is required. For example, in endoscopically placed stents, the sheath tends to prevent or obscure the location of the stent, making accurate placement of the stent more difficult.

Further potential drawbacks for the conventional sheathed stent delivery system involve the stent placement within the system prior to use within a patient. Loading and anchoring of a conventional sheathed stent delivery device is an involved process that may require preloading the stent into the device so that the stent remains compressed within the sheath during shipment and storage prior to use in the patient. Extended compression of the stent may lead to an alteration in the stent mechanical properties.

Conventional sheathed stent delivery devices also require a high force to overcome the friction between the stent and the sheath that may also be a problem for proper stent placement within the patient. The introducer must be mechanically stronger to overcome the frictional forces to avoid undesirable frictional consequences such as stretching of the introducer catheters and hysteresis in the movement of the stent. The sheathed stent delivery device also requires more space within an endoscope compared to a sheathless device and also adds additional expense to the delivery system.

A longitudinally tensioned stent delivery system has been developed to avoid some of the drawbacks that can occur with a sheathed delivery device described above. The longitudinally tensioned stent delivery system includes an inner and an outer shaft coaxially positioned and longitudinally moveable in relation to each other to expand and constrain a stent positioned on the inner and outer shafts that can increase the control, accuracy and ease of placement of a stent during deployment of the stent within a patient. A handle control system for controlling the movement of the inner and outer shafts relative to each other is needed to control the longitudinally tensioned stent delivery system to provide the ability to deliver the stent to the desired position and to be able to reconstrain, recapture, reposition and/or remove the stent after expansion of the stent.

SUMMARY OF THE INVENTION

Accordingly, it is an object of the present invention to provide a device and a method having features that resolve or improve on one or more of the above-described drawbacks.

The foregoing object is obtained in one aspect of the present invention by providing a control system for controlling movement of a medical device delivery system having a first shaft and a second shaft, the first shaft is movable relative to the second shaft. The control system includes a rotatable gear having a plurality of protrusions. The system further includes a first movable member operably connected to the gear and the first shaft and a second movable member operably connected to the gear and the second shaft. Rotation of the rotatable gear moves the first movable member relative to the second movable member to change a position of the first shaft relative to the second shaft and to change a configuration of a medical device operably connected to the first shaft and the second shaft.

In another aspect of the present invention, a stent delivery system is provided. The stent delivery system includes a first shaft and a second shaft, the second shaft movable relative to the first shaft and coaxially extending with the first shaft. The stent delivery system also includes a stent operably connected to the first shaft and the second shaft; and a control system. The control system includes a rotatable gear, a first movable member operably connected to the gear and the first shaft and a second movable member operably connected to the gear and the second shaft. Rotation of the rotatable gear moves the first movable member relative to the second movable member to change a position of the first shaft relative to the second shaft and to change the stent operably connected to the first shaft and the second shaft from a constrained configuration to an expanded configuration.

In another aspect of the present invention, a method for delivering a medical device using a medical device delivery system is provided. The method includes providing a control system. The control system includes a rotatable gear, a first movable member operably connected to the gear and the first shaft and a second movable member operably connected to the gear and the second shaft. The method further includes activating the rotatable gear, moving the first movable member and the second movable member, and changing the position of the first shaft relative to the second shaft. The method further includes changing a configuration of a medical device connected to the first shaft and the second shaft when the first shaft is moved relative to the second shaft.

DETAILED DESCRIPTION OF THE EMBODIMENTS

Figure 1:
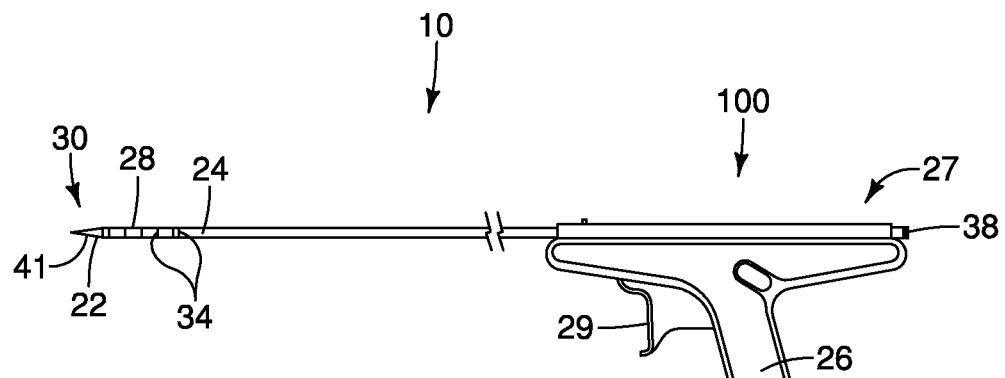
FIG. 1 is a side view of a stent delivery system.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the stent to a patient. Hence the term "distal" means the portion of the delivery system that is farthest from the physician and the term "proximal" means the portion of the delivery system that is nearest to the physician.

FIG. 1 illustrates an exemplary stent delivery system 10 that may be provided with a handle system 100 for controlling the stent delivery system 10 according to an embodiment of the present invention. The delivery system 10 may be provided as an over-the-wire configuration or a rapid exchange configuration. The stent delivery system 10 includes an inner shaft 22, an outer shaft 24 and a handle portion 26 at a proximal portion 27 of the system 10. The handle portion 26 may also include an actuator, such as trigger 29 for actuating the handle system 100. The stent delivery system 10 also includes a stent 28 at a distal portion 30 of the delivery system 10. One or more radiopaque markers 34 may be included on the delivery system 10 to indicate the position of the stent 28. The stent delivery system 10 may also include a guide wire (not shown) extendable through a port 38 of the inner shaft 22 through a distal tip 41 at the distal portion 30 of the delivery system 10.

Figure 2:
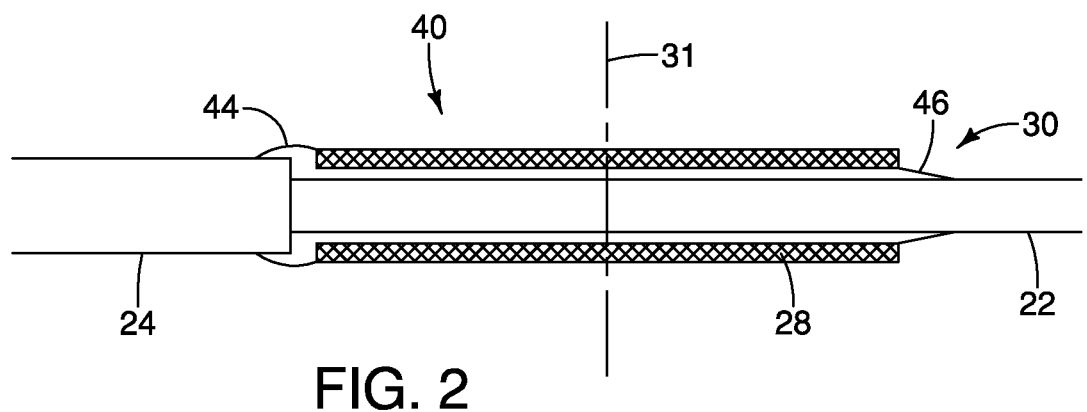
FIG. 2 is a sectional view of a distal portion of the delivery system shown in FIG. 1 showing the stent in a constrained configuration.
Figure 3:
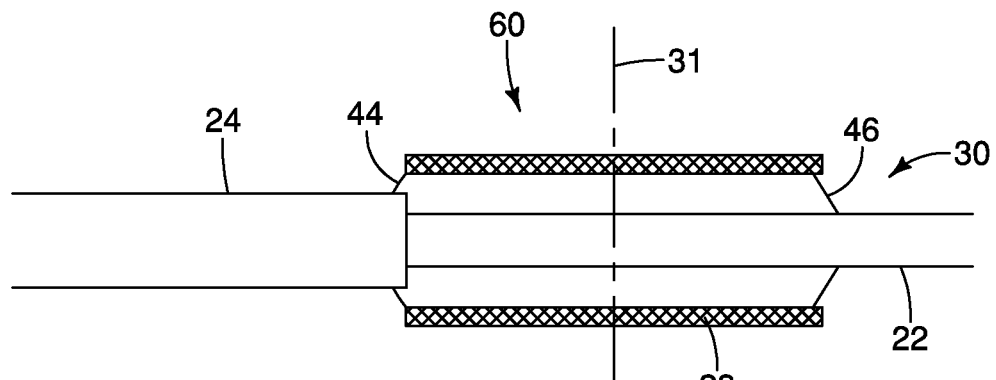
FIG. 3 is a sectional view of a distal portion of the delivery system shown in FIG. 1 showing the stent in an expanded configuration.

FIGS. 2 and 3 illustrate a distal portion 30 of an exemplary stent delivery system 10 that may be driven by a handle control system in accordance with embodiments of the present invention. The inner shaft 22 and the outer shaft 24 of the stent delivery system 10 are longitudinally movable with respect to each other to facilitate the placement of the stent 28. The inner shaft 22 and the outer shaft 24 may be coaxially positioned and movable relative to each other. The stent 28 may be connected to the inner shaft 22 by a distal constraining member 46 and to the outer shaft 24 by a proximal constraining member 44. The stent 28 is movable between a constrained configuration 40 shown in FIG. 2 and an expanded configuration 60 shown in FIG. 3. As shown in FIG. 2, the inner shaft 22 is moved distally and the outer shaft 24 is moved proximally to position the stent 28 in the constrained configuration 40. As shown in FIG. 3, the inner shaft 22 is moved proximally and the outer shaft 24 is moved distally to expand the stent 28 from the constrained configuration 40 to the expanded configuration 60. The embodiment of the distal portion 30 of the delivery system 10 is shown by way of example and meant to be non-limiting. Other configurations for the arrangement of the connection of the stent to the inner and outer shafts for moving the stent between the constrained and expanded configurations are also possible. In some embodiments, one of the inner shaft 22 and the outer shaft 24 may be moved relative to the other of the inner shaft 22 and the outer shaft 24 to move the stent between the constrained configuration 40 and the expanded configuration 60.

In some embodiments, the stent 28 may be a self-expanding stent and may be configured—for example—as an esophageal stent. The stent 28 may be any kind of stent that has a tendency to radially collapse when a longitudinal force is applied to the ends of the stent proximally and distally outward along its central longitudinal axis (centerline). By way of non-limiting example, the stent 28 may be formed as a woven mesh formed from a metal or polymer or a laser cut pattern formed in a metal stent. The stent may also be formed from a bioabsorbable material. One example of a woven stent is the EVOLUTION® stent (Wilson-Cook Medical, Inc.)

As shown in FIG. 3, the proximal and distal constraining members 44, 46 remain connected to the stent 28 in the expanded configuration 60. The connection allows the stent 28 to be moved from the expanded configuration 60 to the constrained configuration 40 so that the stent 28 is recollapsed onto the inner shaft 22 by moving the inner shaft 22 relative to the outer shaft 24 by moving the handle control system 100 as explained in more detail below. The inner shaft 22 and the outer shaft 24 are moved relative to each other so that the proximal and distal constraining members 44, 46 are spaced further apart and the longitudinal tension is returned to the stent 28 to collapse the stent onto the inner shaft 22. The stent 28 may be repeatedly moved between the constrained configuration 40 and the expanded configuration 60 by moving the control system 100 until the stent is properly positioned. With the stent repositioned in the constrained configuration 40, an optional outer sheath 32 may be repositioned over the stent 28 (not shown) and the stent 28 may even be withdrawn from the patient, for example if an incorrect size of stent was originally selected. The stent configurations may be changed multiple times within the patient for repositioning or removal until the proximal and distal constraining members 44, 46 are released from connection with the stent 28 as described below.

Figure 4A:
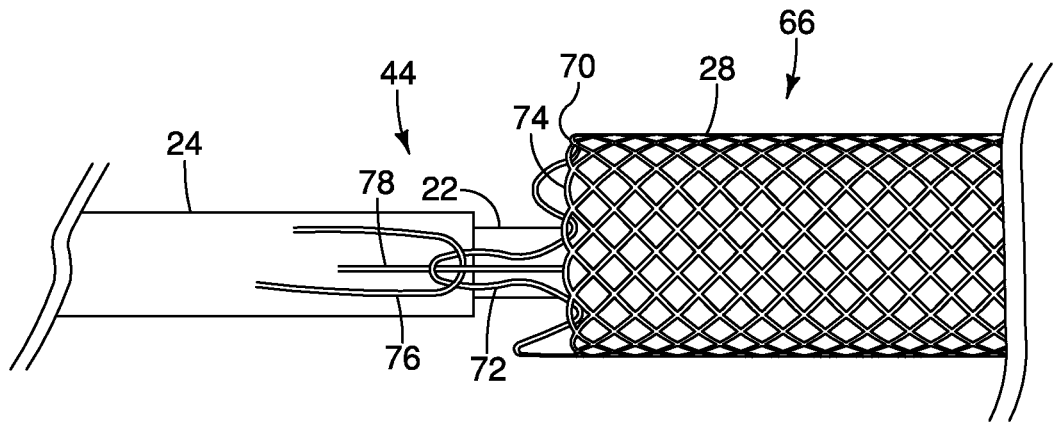
FIG. 4A is a partial side view of a proximal portion of the stent and the device shown in FIG. 3 illustrating a proximal constraining member.
Figure 4B:
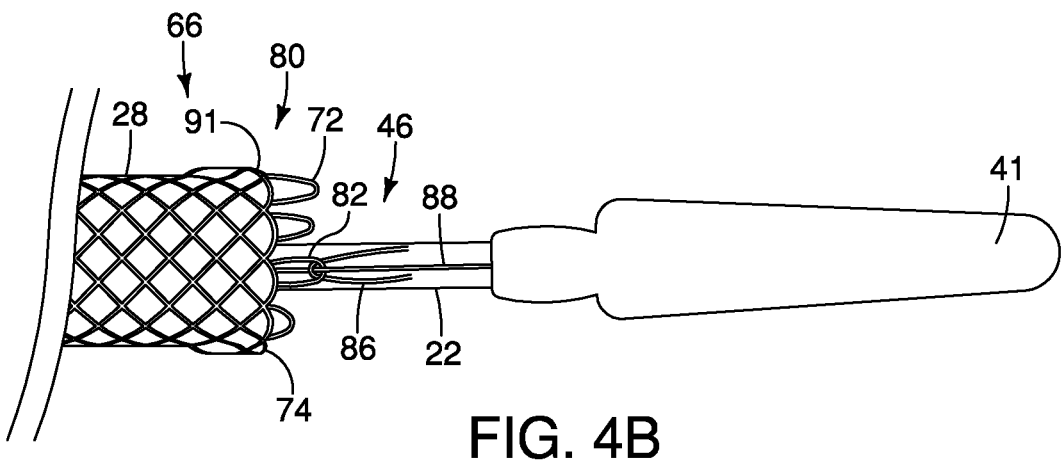
FIG. 4B is a partial side view of a distal portion of the stent and the device shown in FIG. 3 illustrating a distal constraining member.
Figure 4C:
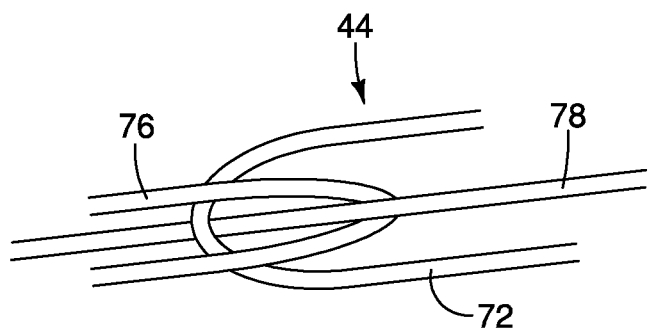
FIG. 4C is an enlarged view of a constraining member according to an embodiment of the present invention.

FIGS. 4A-4C illustrate an exemplary embodiment of a proximal constraining member 44 (FIG. 4A) and a distal constraining member (FIG. 4B). An exploded view of the components of the proximal constraining member 44 is shown in FIG. 4C and the components of the distal constraining member 46 may be a mirror image of the components of the proximal constraining member 44 (not shown). As shown in FIG. 4A, a proximal end portion 70 of the stent 28 remains connected to the inner shaft 22 even in the expanded configuration 60 using the proximal constraining member 44 in combination with the distal constraining member 46. The proximal constraining member 44 may include a first loop 72 that may be interwoven through one or more peaks 74 of the stent 28 so that the first loop 72 when pulled taught will collapse the peaks 74 of the stent 28 onto the inner shaft 22. The proximal constraining member 44 may further include a second retaining loop 76 that may be attached to the outer shaft 24.

The proximal constraining member 44 may also include a proximal retaining wire 78 that is configured to cooperate with the first loop 72 and the second retaining loop 76 to releasably lock the first loop 72 to the second retaining loop 76 to allow selective expansion and contraction of the stent 28 in cooperation with the distal constraining member 46. The first loop 72, the second loop 76 or both may be anchored at one or more points to better secure the stent 28 on the inner catheter 22, for example in a system 10 that is provided without a sheath. In some embodiments, the first loop 72 may be wound around the inner catheter 22 or the outer shaft 24 to facilitate holding the stent to the inner catheter 22 as the delivery system 10 is advanced to the treatment site through a curve, for example through an elevator of a duodenal endoscope.

An exemplary cooperative configuration of the proximal constraining member 44 is shown in FIG. 4C where a portion of the first loop 72 and the second retaining loop 76 are overlapping and the proximal retaining wire 78 extends through the overlapping loops 72, 76 to releasably hold the two loops 72, 76 together. The proximal retaining wire 78 shown in FIG. 4A may be frictionally engaged with a portion of the outer shaft 24 to hold the proximal retaining wire 78 in position until the stent 28 is in the proper position for release as discussed above. The proximal retaining wire 78 may be proximally withdrawn to release the proximal constraining member 44 and to completely release the stent 28 from connection to the inner shaft 22.

As shown in FIG. 4B, a distal end portion 80 of the stent 28 may remain connected the inner shaft 22 even in the expanded configuration 66 using the distal constraining member 46. The distal constraining member 46 may include a first loop 82 that may be interwoven through one or more peaks 74 of the stent 28 so that the first loop 82 when pulled taught will collapse the peaks 74 of the stent 28 onto the outer shaft 24. The distal constraining member 46 may further include a second retaining loop 86 that may be attached to the inner shaft 22. The first loop 82, the second loop 86 or both may be anchored at one or more points to better secure the stent 28 on the inner catheter 22, for example in a system 10 that is provided without a sheath. In some embodiments, the first loop 82 may be wound around the inner catheter 22 or the outer shaft 24 to facilitate holding the stent to the inner catheter 22 as the delivery system 10 is advanced to the treatment site through a curve similar to the loop 72 described above.

The distal constraining member 46 may also include a distal retaining wire 88 that is configured to cooperate with the first loop 82 and the second retaining loop 86 to releasably hold the loops 82, 86 together to allow selective expansion and contraction of the stent 28. The distal retaining wire 88 may be frictionally engaged with the inner shaft 22 or the distal tip 41 to hold the distal retaining wire 88 in position until the stent 28 is properly positioned for release. The distal constraining member 46 may be configured similarly to the proximal constraining member 44 shown in FIG. 4C with the distal retaining wire 88 releasably locking the first loop 82 and the second retaining loop 86 together. The distal retaining wire 88 may be proximally withdrawn to release the distal constraining member 46 and to completely release the stent 28 from connection to the inner shaft 22.

The proximal and distal retaining wires 78, 88 may be connected to the handle 26 for proximal withdrawal from the loops 72, 76, 82, 86. The withdrawal of the proximal and distal retaining wires 78, 88 may be simultaneous or sequential. Because the stent 28 has been positioned in the proper position within the lumen of the patient by equal and opposite movement of the handle 26 allowing the stent 28 to move to the expanded configuration 60, the timing of the release of the retaining wires 78, 88 is not critical for the positioning of the stent 28. As will be understood by one skilled in the art, the proximal constraining member 44 may be connected to the inner catheter 22 and the distal constraining member 46 may be connected to the outer catheter 24. In embodiments provided without the outer sheath 32, the peaks 74 of the stent 28 are collapsed closely against the inner catheter 22 at both ends of the stent 28 for delivery to the patient site.

While the proximal and distal restraining members 44, 46 have been described with reference to connection to the proximal and distal end portions 70, 80 of the stent 28, it is also possible to provide proximal and distal constraining members 44, 46 that are connected to other portions of the stent 28 and still provide a constrained configuration 40 for the stent 28. For example, the proximal constraining member may be connected to a mid proximal portion or mid-point of the stent and the distal constraining member may be connected to the distal end portion of the stent. Similarly, the proximal constraining member may be connected to the proximal end portion of the stent and the distal constraining member may be connected to the midpoint of mid distal portion of the stent or both the proximal and distal constraining members may be connected to other than the proximal and distal end portions of the stent. In some embodiments, the proximal or the distal constraining members or both proximal and distal constraining members may be connected to the stent at a plurality of positions on the stent. Other types of constraining members may also be used with the stent delivery system 10 and may be similarly controlled by the handle control system 100 described below.

Figure 5:
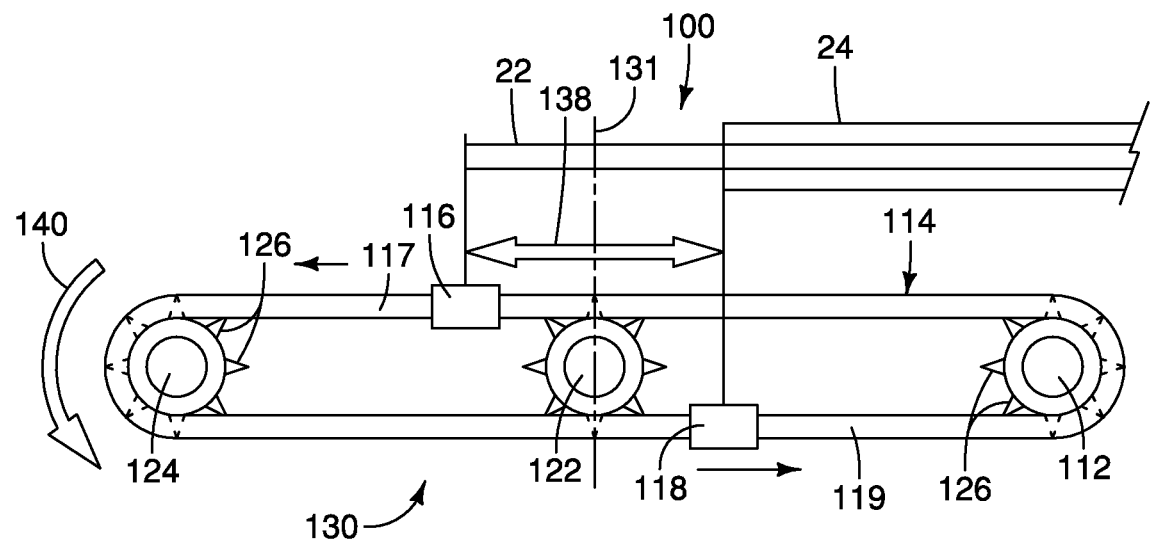
FIG. 5 is a side view of an embodiment of a handle control system in a first position.
Figure 6:
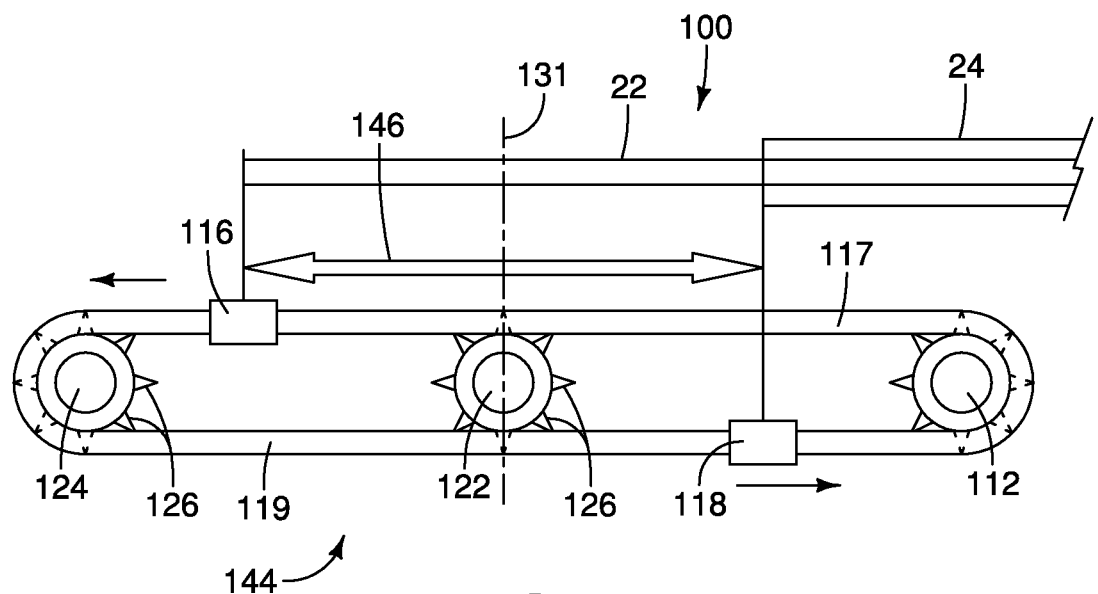
FIG. 6 is a side view of the handle control mechanism shown in FIG. 5 in a second position.
Figure 13:
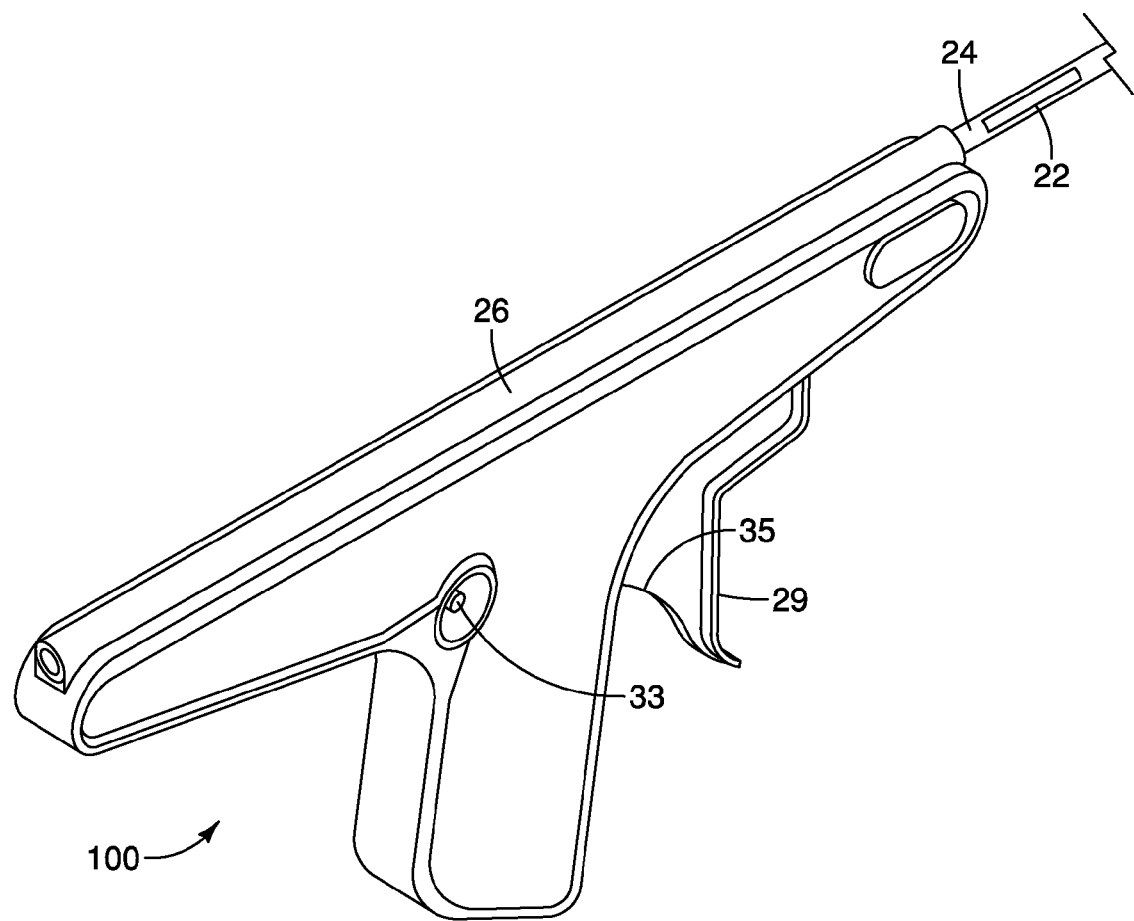
FIG. 13 is a perspective view of a handle.

An embodiment of a handle control system 100 is shown FIGS. 5 and 6. The handle control system 100 may be provided to facilitate the manipulation of a medical device. The handle control system 100 may be provided as part of the handle 26 at the proximal portion 27 of the stent delivery system 10 (See FIGS. 1 and 13). As shown in FIGS. 5 and 6, the handle control system 100 includes a first rotatable gear 112 connected to a belt 114. The gear may be any type of gear known to one skilled in the art and also may includes pulleys.

Figure 7:
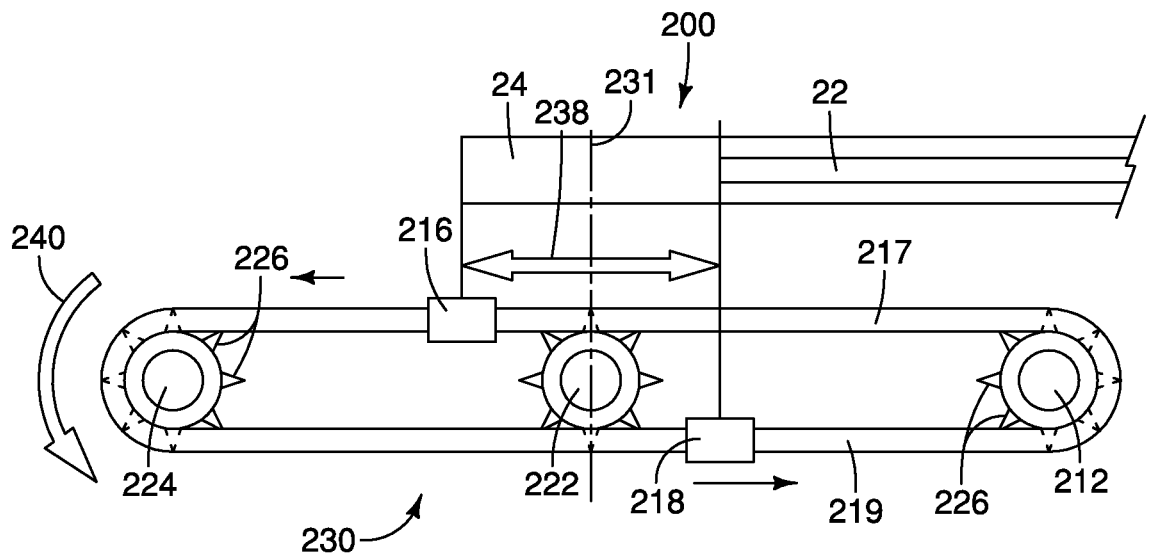
FIG. 7 is a side view of an alternative embodiment of a handle control mechanism in a first position.
Figure 8:
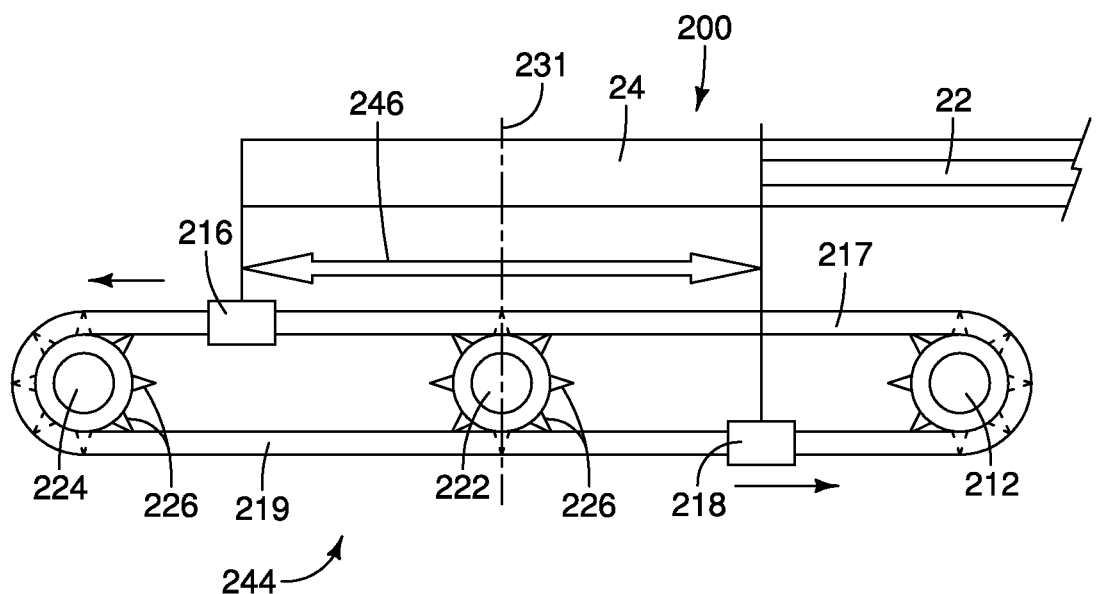
FIG. 8 is a side view of the handle control mechanism shown in FIG. 7 in a second position.

A first movable member 116 operably connects the belt 114 and the inner shaft 22. A second movable member 118 operably connects to the belt 114 and the outer shaft 24. The belt 114 may form a loop having an upper portion 117 and a lower portion 119 such that the upper portion 117 and the lower portion 119 extend substantially parallel to each other. The first movable member 116 may be positioned on the upper portion 117 of the belt 114 and the second movable member 118 may be positioned on the lower portion 119 of the belt 114. When the belt 114 is rotated by the gear 112, for example in a clockwise direction, the movable members 116, 118 move with the belt 114 and the inner and outer shafts 22, 24 move in opposite directions. FIGS. 7 and 8 illustrate an alternate operable connection for the inner and outer shafts 22, 24.

The handle control system 100 may also include one or more additional rotatable gears 122, 124 as shown in FIG. 5. Each of the rotatable gears 112, 122, 124 may include a plurality of teeth 126 that operably connect to the belt 114 to move the belt 114 and the movable members 116, 118. The belt 114 may be provided as a chain having openings to receive the teeth 126 as the gears 112, 122, 124 rotate to move the belt 114. As shown in FIGS. 5 and 6, the handle control system 100 is movable about a central position indicated by the axis 131. One gear 122 may be centrally positioned relative to the axis 131, however, the gears 112, 122, 124 may be positioned anywhere relative to the central axis 131. A driving force may be generated at any position on the belt 114, for example at one or more of the gears 112, 122, 124.

FIG. 5 illustrates a first position 130 for the handle control system 100. In the embodiment shown, the first position 130 corresponds to the constrained configuration 40 for the stent 28 shown in FIG. 2. In the first position 130, the first and second movable members 116, 118 are a first distance 138 apart. At least one gear 112 drives the belt 114 in a first direction 140 indicated by the arrow in FIG. 5 so that the handle control system 100 is moved to a second position 144 shown in FIG. 6. Movement of the belt 114 to the second position 144 moves the first movable member 116 and the inner shaft 22 proximally and the second movable member 118 and the outer shaft 24 distally relative to the central axis 131. The first and second movable members 116, 118 are a second distance 146 apart in the second position 144. The second position 146 of the handle control system 100 corresponds to the expanded configuration 60 for the stent 28 shown in FIG. 3. The pitch circle diameter of the gear 112 may be adjusted to control the force and speed of deployment of the medical device.

As shown in FIGS. 5 and 6, the movement of the first and second moveable members 116, 118 relative to the central axis 131 is equal and opposite. The belt 114 operably drives the inner and outer shafts 22, 24 in equal and opposite directions so that the longitudinal tension on the stent 28 is applied or removed with substantially equal force on both ends of the stent 28. As shown in FIGS. 2 and 3, when equal and opposite force is applied to and removed from the stent 28, a central portion 31 of the stent 28 remains in the same position as the stent 28 is moved between the constrained configuration 40 and the expanded configuration 60. The movable members 116, 118 may be returned to the first position 130 from the second position 144 by moving at least one gear 112 and the belt 114 in the opposite direction so that the first movable member 116 and the inner shaft 22 move distally and the second movable member 118 and the outer shaft 24 move proximally relative to the central axis 131. The movable members 116, 118 may be moved between the first position 130 and the second position 144 multiple times to move the stent 28 between the constrained configuration 40 and the expanded configuration 60 until the stent 28 is properly positioned for release at the treatment site.

An alternative embodiment of a handle control system 200 is shown FIGS. 7 and 8. The handle control system 200 is similar to the handle control system 100 and may be provided as part of the handle 26 at the proximal portion 27 of the stent delivery system 10 (See FIG. 1). As shown in FIGS. 7 and 8, the handle control system 200 includes a first rotatable gear 212 connected to a belt 214. A first movable member 216 operably connects the belt 214 and the outer shaft 24. A second movable member 218 operably connects to the belt 214 and the inner shaft 22. The belt 214 may form a loop having an upper portion 217 and a lower portion 219 such that the upper portion 217 and the lower portion 219 extend substantially parallel to each other. The first movable member 216 may be positioned on the upper portion 217 of the belt 214 and the second movable member 218 may be positioned on the lower portion 219 of the belt 214. When the belt 214 is rotated by the gear 212, for example in a clockwise direction, the movable members 216, 218 move with the belt 214, i.e. clockwise or counter clockwise, and the inner and outer shafts 22, 24 move in opposite directions.

The handle control system 200 may also include one or more additional rotatable gears 222, 224 as shown in FIG. 7. Each of the gears 212, 222, 224 may include a plurality of teeth 226 that operably connect to the belt 214 to move the belt 214 and the movable members 216, 218. The belt 214 may be provided as a chain having openings to receive the teeth 226 as the gears 212, 222, 224 rotate to move the belt 214. The pitch circle diameter of the gear 212, 222, 224 may be adjusted to control the force and speed of deployment of the medical device.

As shown in FIGS. 7 and 8, the handle control system 200 is movable about a central position indicated by the axis 231. One gear 222 may be centrally positioned relative to the axis 231, however, the gears 212, 222, 224 may be positioned anywhere relative to the central axis 231. A driving force may be generated at any position on the belt 214, for example at one or more of the gears 212, 222, 224.

FIG. 7 illustrates a first position 230 for the handle control system 200. In the embodiment shown, the first position 230 corresponds to the expanded configuration 60 for the stent 28 shown in FIG. 3. In the first position 230, the first and second movable members 216, 218 are a first distance 238 apart. At least one rotatable gear 212 drives the belt 214 in a first direction 240 indicated by the arrow in FIG. 7 so that the handle control system 200 is moved to a second position 244 shown in FIG. 8. Movement of the belt 214 to second position 244 moves the first movable member 216 and the outer shaft 24 proximally and the second movable member 218 and the inner shaft distally relative to the central axis 231. The first and second movable members 216, 218 are a second distance 246 apart in the second position 244. The second position 246 of the handle control system 200 corresponds to the constrained configuration 40 for the stent 28 shown in FIG. 2.

As shown in FIGS. 7 and 8, the movement of the inner and outer shafts 22, 24 relative to the central axis 231 is equal and opposite. The belt 214 drives the first and second movable members 216, 218 so that the longitudinal tension on the stent 28 is applied or removed with substantially equal force on both ends of the stent 28. As shown in FIGS. 2 and 3, when equal and opposite force is applied to and removed from the stent 28, a central portion 31 of the stent 28 remains in the same position as the stent 28 is moved between the constrained configuration 40 and the expanded configuration 60. The movable members 216, 218 may be returned to the first position 230 from the second position 244 by moving the at least one gear 212 and the belt 214 in the opposite direction so that the first movable member 216 and the outer shaft 24 move distally and the second movable member 218 and the inner shaft 22 move proximally. The movable members 216, 218 may be moved between the first position 230 and the second position 244 multiple times to move the stent 28 between the constrained configuration 40 and the expanded configuration 60 until the stent 28 is properly positioned for release at the treatment site.

The handle control system 100, 200 may be controlled by the trigger 29 of the handle 26 and will be described with reference to the system 100. Squeezing the trigger 29 may cause the gear 112 to rotate and move the belt 114 in the first direction 140. The operation of the trigger 29 may be set so that a single pull of the trigger 29 moves the movable members 116, 118 from the first position 130 to the second position 144. Alternatively, multiple pulls of the trigger 29 may be used to move the movable members 116, 118 from the first position 130 to the second position 144. The handle 26 may also include a button 33 to reverse the direction that the belt 114 moves, for example by driving a different gear 122 is a second, opposite direction to the first direction 130. The movable members 116, 118 may be returned to the first position 130 from the second position 144. The handle 26 may include a lock 35 that can lock the movable members 116, 118 in any positioned desired. For example, the lock 35 may be activated to lock the movable members in the second position 144 with the stent 28 in the expanded configuration 60 so that the stent 28 can be released finally from the constraining members 44, 46 once the stent is properly positioned. Additional gears may be provided to drive the handle control system 100. An exemplary gear system that may be provided to drive the belt 114 is described in U.S. Publication 2009/0024133, which is incorporated by reference herein in its entirety. Additional handles and controls for driving the belt 114 may also be used with the handle control system described herein.

Figure 9:
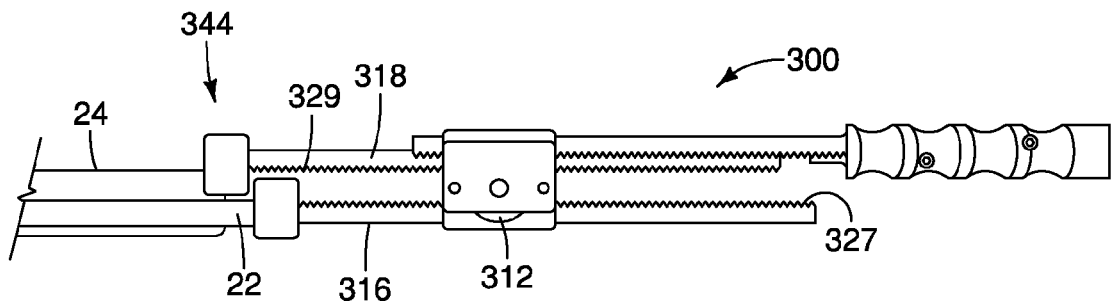
FIG. 9 is a side view of an embodiment of a handle control system in a second position.
Figure 10:
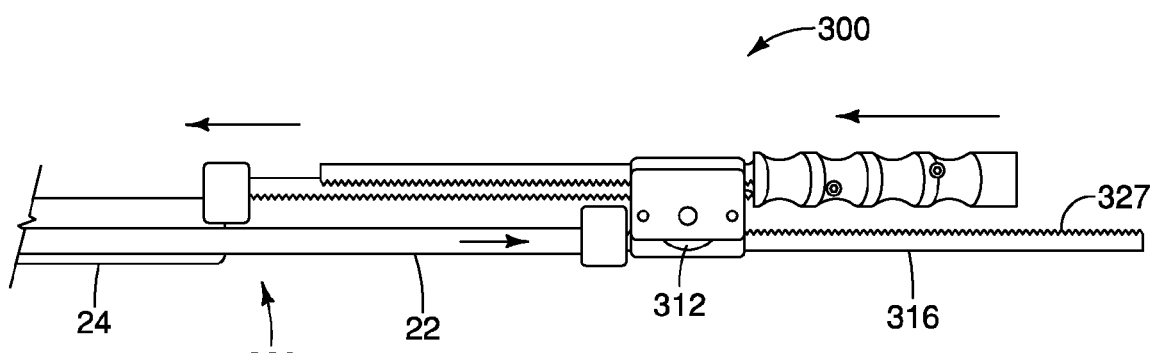
FIG. 10 is a side view of an embodiment of a handle control system in a first position.

An alternative embodiment of a handle control system 300 is shown FIGS. 9-12. The handle control system 300 may be provided to facilitate the manipulation of a medical device. The handle control system 300 may be provided as part of the handle 26 at the proximal portion 27 of the stent delivery system 10 (See FIG. 1). As shown in FIGS. 9 and 10, the handle control system 300 includes a first rotatable gear 312. The gear may be any type of gear known to one skilled in the art and also may includes pulleys. A first movable member 316 operably connects the gear 312 and the inner shaft 22. A second movable member 318 operably connects to the gear 312 and the outer shaft 24. The first and second movable members 316, 318 are longitudinally movable relative to each other and can be moved by the gear 312. For example, if the gear 312, is rotated in a clockwise direction, the movable members 316, 318 move relative to each other and the inner and outer shafts 22, 24 move in opposite directions.

Figure 11:
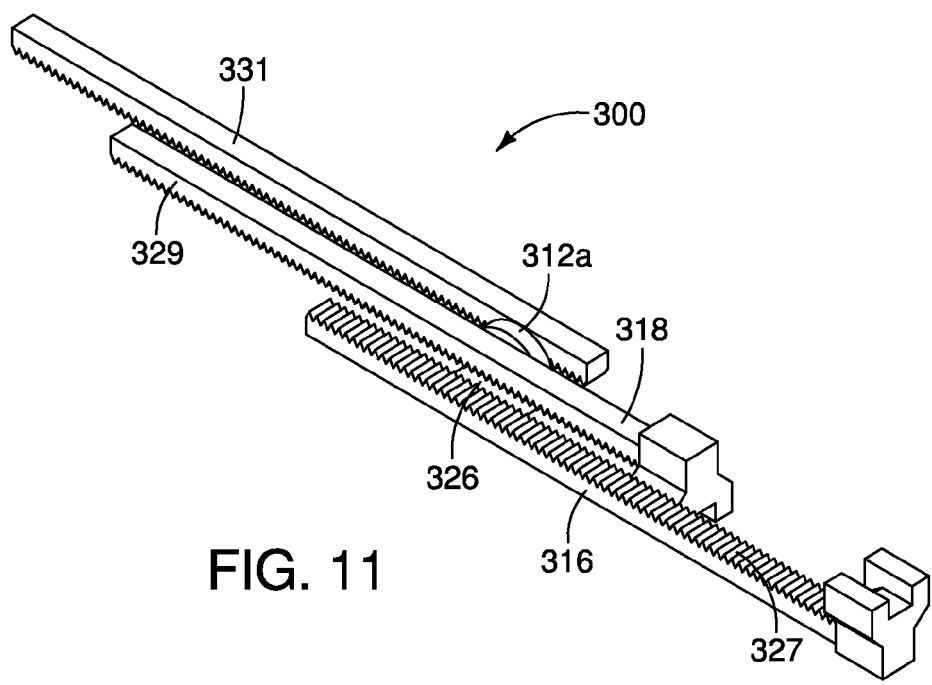
FIG. 11 is a perspective view of an embodiment of a handle control system.

The handle control system 300 may also include one or more additional rotatable gears or a double gear 312a as shown in FIG. 11. Each of rotatable gear 312 may include a plurality of teeth 326 that operably connect to teeth 327 on the first movable member 316 and teeth 329 on the second moveable member 318.

FIG. 10 illustrates a first position 330 for the handle control system 300. In the embodiment shown, the first position 330 corresponds to the constrained configuration 40 for the stent 28 shown in FIG. 2. The movable members 316, 318 are movable relative to move the handle control system 300 to a second position 344 shown in FIG. 9. Movement of handle control system 300 to the second position 344 moves the first movable member 316 and the inner shaft 22 and the second movable member 318 and the outer shaft 24 in opposite directions. The second position 344 of the handle control system 300 corresponds to the expanded configuration 60 for the stent 28 shown in FIG. 3. The pitch circle diameter of the gear 312 may be adjusted to control the force and speed of deployment of the medical device.

The movement of the first and second moveable members 316, 318 relative to the gear 312 may be equal and opposite. As shown in FIGS. 2 and 3, when equal and opposite force is applied to and removed from the stent 28, a central portion 31 of the stent 28 remains in the same position as the stent 28 is moved between the constrained configuration 40 and the expanded configuration 60. The movable members 316, 318 may be returned to the first position 330 from the second position 344 by moving at least one gear 312 in the opposite direction so that the first movable member 316 and the inner shaft 22 and the second movable member 318 and the outer shaft 24 move in opposite directions. The movable members 316, 318 may be moved between the first position 330 and the second position 344 multiple times to move the stent 28 between the constrained configuration 40 and the expanded configuration 60 until the stent 28 is properly positioned for release at the treatment site.

Figure 12:
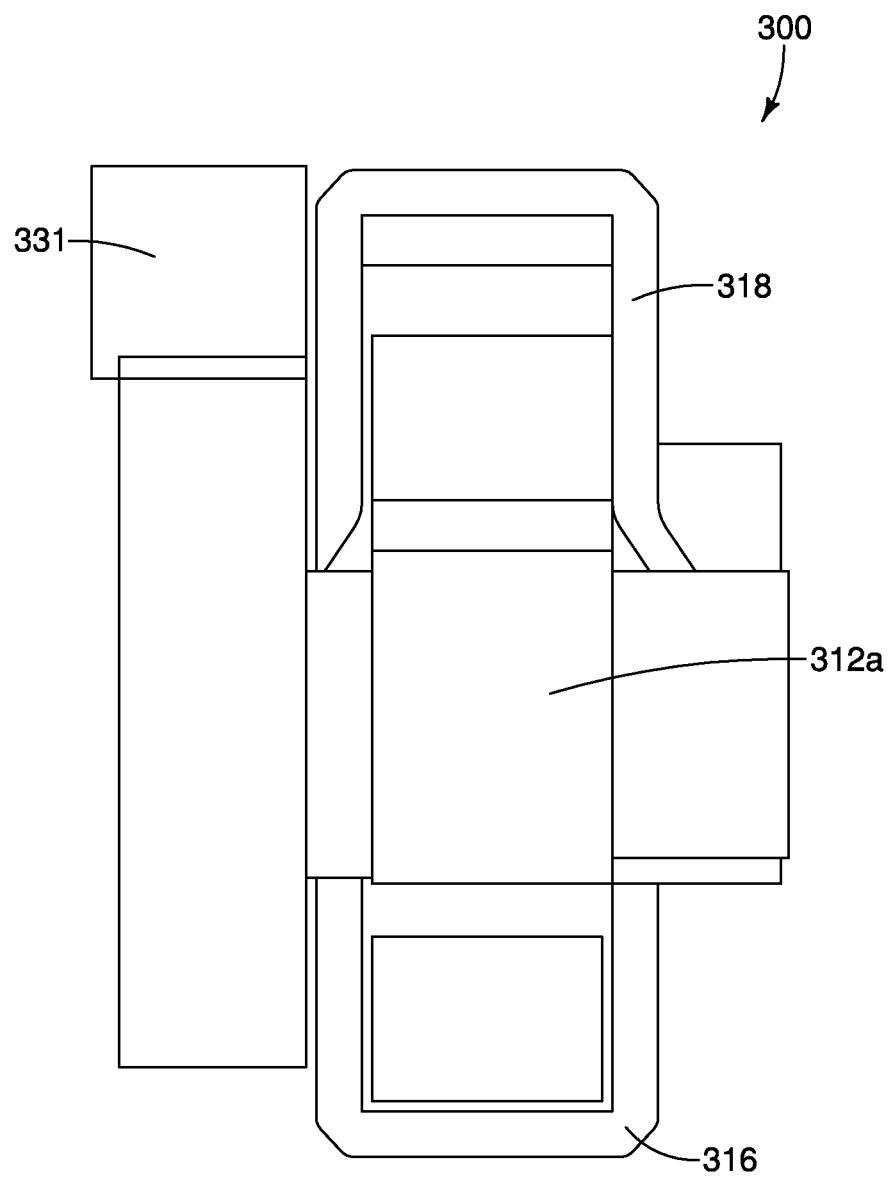
FIG. 12 is an end view of the handle control system shown in FIG. 11.

FIG. 11 illustrates a perspective view of the handle control system 300. As shown in FIG. 11, the handle control system 300 may also include a stationary member 331 and a double gear 312a. The stationary member 331 may be provided to create additional gearing to control the speed and the force of the deployment of the medical device. FIG. 12 illustrates an end view of the device shown in FIG. 11.

The handle control system 100, 200, 300 allows the stent delivery system 10 to be stored and shipped within a sterile packaging and provided to the end user with the stent 28 in either the expanded configuration 60 or the constrained configuration 40. For example, some stent materials may weaken or otherwise deform when stored in the constrained configuration 40 with the longitudinal tension exerting force on the stent during shipping and storage. By way of non-limiting example, the stent 28 may be operably connected to the inner and outer shafts 22, 24 by the proximal and distal constraining members 44, 46 and shipped in the sterile packaging in the expanded configuration 60. The handle control system 100, 200 allows the end user to receive the stent delivery system 10 with the stent 28 in the expanded configuration 60 and then by moving the handle control system 100 to the first position 130 or by moving the handle control system 200 to the second position 244, the stent 28 may be moved to the constrained configuration 40 for delivery to the treatment site within the patient. Similar positions for the handle control system 300 may be also used. In some embodiments, the stent 28 may be shipped and stored in the constrained configuration 40 so that the stent 28 is ready to be delivered to the treatment site upon receipt by the end user.

The materials used to manufacture the components of the stent delivery systems described herein may be any materials known to one skilled in the art that are suitable for use in patients. By way of non-limiting example, the shafts and sheaths may be formed from polytetrafluoroethylene (PTFE) particularly when a low friction outer sheath is desirable. Nylon and HDPE may also be used for clarity. Additional possible materials include, but are not limited to the following, polyethylene ether ketone (PEEK), fluorinated ethylene propylene (FEP), perfluoroalkoxy polymer resin (PFA), polyamide, polyurethane, high density or low density polyethylene, and nylon including multi-layer or single layer structures and the like and may also include reinforcement wires, braid wires, coils, coil springs and or filaments.

The stent may be formed from but is not limited to the following materials: Nickel titanium alloys, for example, nitinol, stainless steel, cobalt alloys and titanium alloys. The loops of the constraining members may be made from common suture material as known in the art, for example polyester suture such as 4-0 Tevdek®, nylon, silk, polypropylene, ultra high molecular weight polyethylene (UHMWPE) and the like. The sutures may be monofilament, braided, twisted or multifilament. The loops and the retaining wires may also be made from a metallic alloy such as stainless steel or nickel titanium. In some embodiments, the stent, the loops and/or the retaining wires may be made from biodegradable materials. A number of bioabsorbable homopolymers, copolymers, or blends of bioabsorbable polymers are known in the medical arts. These include, but are not necessarily limited to, polyesters including poly-alpha hydroxy and poly-beta hydroxy polyesters, polycaprolactone, polyglycolic acid, polyether-esters, poly(p-dioxanone), polyoxaesters; polyphosphazenes; polyanhydrides; polycarbonates including polytrimethylene carbonate and poly(iminocarbonate); polyesteramides; polyurethanes; polyisocyanates; polyphosphazines; polyethers including polyglycols, polyorthoesters; epoxy polymers including polyethylene oxide; polysaccharides including cellulose, chitin, dextran, starch, hydroxyethyl starch, polygluconate, hyaluronic acid; polyamides including polyamino acids, polyester-amides, polyglutamic acid, poly-lysine, gelatin, fibrin, fibrinogen, casein, collagen.

Other suitable biocompatible materials may also be used for any of the components described herein.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A control system for controlling movement of a medical device delivery system having a first shaft and a second shaft, the first shaft movable relative to the second shaft, the first shaft and the second shaft connected to a medical device, the medical device having a first configuration and a second configuration, the control system comprising:
    a rotatable gear, the rotatable gear comprising a plurality of protrusions;
    a first movable member operably connected to the gear and the first shaft; and
    a second movable member operably connected to the gear and the second shaft;
    wherein rotation of the rotatable gear moves the first movable member relative to the second movable member in opposite directions and an equal distance from a central axis of the control system to change a position of the first shaft relative to the second shaft and equal and opposite force is removed from the medical device to change the medical device from the first configuration to the second configuration.

2. The control system of claim 1, comprising a belt having a plurality of openings operably connected to the plurality of protrusions so that the belt is movable by the rotatable gear, the first and second movable members operably connected to the belt.

3. The control system of claim 2, wherein the first movable member and the second movable member are operably connected to the belt in a position so that the first shaft moves in an opposite direction relative to the second shaft.

4. The control system of claim 1, wherein the control system is movable from a first position to a second position, the distance between the first and second movable members relative to a central axis of the control system is greater in the second position than in the first position.

5. The control system of claim 1, wherein the first shaft extends coaxially with the second shaft.

6. The control system of claim 1, wherein the control system comprises a plurality of rotatable gears.

7. The control system of claim 1, wherein the medical device comprises a stent having a first portion operably connected to the first shaft and a second portion operably connected to the second shaft, wherein movement of the first shaft relative to the second shaft moves the stent from a constrained configuration to an expanded configuration.

8. The control system of claim 7, wherein the stent is repeatedly movable between the constrained configuration and the expanded configuration.

9. The control system of claim 1, wherein the first movable member and the second movable member each comprise a plurality of protrusions configured to mate with the plurality of protrusions of the rotatable gear to facilitate movement of the first shaft relative to the second shaft.

10. The control system of claim 2, wherein the belt is movable in a first direction and a second direction.

11. The control system of claim 2, wherein the belt forms a loop having an upper portion and a lower portion, the upper portion and the lower portion extending substantially parallel to each other.

12. The control system of claim 11, wherein the first movable member is operably connected to the upper portion and the second movable member is operably connected to the lower portion.

13. A stent delivery system comprising:
    a first shaft;
    a second shaft, the second shaft movable relative to the first shaft and coaxially extending with the first shaft;
    a stent operably connected to the first shaft and the second shaft; and
    a control system comprising:
        a rotatable gear;
        a first movable member operably connected to the gear and the first shaft; and
        a second movable member operably connected to the gear and the second shaft;
    wherein rotation of the rotatable gear moves the first movable member and the second movable member in opposite directions and an equal distance from a central axis of the control system to change a position of the first shaft relative to the second shaft and equal and opposite force is removed from the stent to change a configuration of the stent operably connected to the first shaft and the second shaft from a constrained configuration to an expanded configuration.

14. The delivery system of claim 13, wherein the first movable member and the second movable member are operably connected to the gear in a position so that the first shaft moves in an opposite direction relative to the second shaft.

15. The delivery system of claim 13, wherein the rotatable gear comprises a plurality of teeth and the first and second movable members are operably connect to a belt having a plurality of openings configured to mate with the plurality of protrusions to move the first shaft relative to the second shaft.

16. A method of controlling the movement of a medical device delivery system, the method comprising:
    providing a control system, the control system comprising:
        a rotatable gear, the rotatable gear comprising a plurality of protrusions;
        a first movable member operably connected to the gear and a first shaft; and a second movable member operably connected to the gear and a second shaft;

activating the rotatable gear to move the first movable member relative to the second movable member in opposite directions and an equal distance from a central axis of the control system;

changing the position of the first shaft relative to the second shaft; and changing a configuration of a medical device connected to the first shaft and the second shaft when the first shaft is moved relative to the second shaft and equal and opposite force is applied to or removed from the medical device.

17. The method of claim 16, further wherein the medical device comprises a stent and moving the first shaft relative to the second shaft changes the configuration of the stent to an expanded configuration or a constrained configuration.

18. The method of claim 16, comprising changing a longitudinal tension on the medical device, wherein the medical device comprises a stent operably connected to the first shaft and the second shaft by changing the position of the first shaft relative to the second shaft.

19. The control system of claim 1, wherein a central portion of the medical device remains in a position when ends of the medical device move when the force is removed from the medical device.

20. The method of claim 16, moving ends of the medical device and maintaining a position of a central portion of the medical device when the first shaft is moved relative to the second shaft and equal and opposite force is applied to or removed from the medical device.

* * * * *